(12) United States Patent
Gianotti et al.

(10) Patent No.: US 11,938,286 B2
(45) Date of Patent: Mar. 26, 2024

(54) USABLE-LENGTH-SELECTABLE CATHETER TO TREAT VASCULAR PATHOLOGIES

(71) Applicant: CTI Vascular AG, Neuhausen (CH)

(72) Inventors: Marc Gianotti, Wiesendangen (CH); Ulf Fritz, Tengen (DE)

(73) Assignee: CTI VASCULAR AG, Neuhausen (CH)

( * ) Notice: Subject to any disclaimer, the term of this patent is extended or adjusted under 35 U.S.C. 154(b) by 894 days.

(21) Appl. No.: 16/959,665

(22) PCT Filed: Jun. 26, 2018

(86) PCT No.: PCT/EP2018/067102
§ 371 (c)(1),
(2) Date: Jul. 1, 2020

(87) PCT Pub. No.: WO2019/161941
PCT Pub. Date: Aug. 29, 2019

(65) Prior Publication Data
US 2021/0077789 A1    Mar. 18, 2021

(30) Foreign Application Priority Data
Feb. 26, 2018   (EP) ..................................... 18158627

(51) Int. Cl.
*A61M 25/09* (2006.01)
*A61M 25/00* (2006.01)
*A61M 25/01* (2006.01)

(52) U.S. Cl.
CPC .. *A61M 25/09016* (2013.01); *A61M 25/0133* (2013.01); *A61M 2025/0059* (2013.01);
(Continued)

(58) Field of Classification Search
CPC ........ A61M 25/09016; A61M 25/0133; A61M 2025/0059; A61M 2025/0161;
(Continued)

(56) References Cited

U.S. PATENT DOCUMENTS 4,586,921 A * 5/1986 Berson ................... A61M 19/00
604/512
5,334,147 A * 8/1994 Johnson .............. A61M 25/104
606/194

(Continued)

FOREIGN PATENT DOCUMENTS

| CN | 102316923 A | 1/2012 |
| EP | 1 681 075 A1 | 7/2006 |

(Continued)

*Primary Examiner* — James D Ponton
(74) *Attorney, Agent, or Firm* — Smith Patent, LLC; Chalin A. Smith

(57) ABSTRACT

The current document is directed to usable-length-selectable catheters that employ usable-length-selectable catheters to treat malformations, constrictions, obstructions, lesions, and blockages within patients' blood vessels. The usable length of the shaft of a usable-length-selectable catheter, to which the current application is directed, can be adjusted over a set of lengths prior to and during medical procedures.

21 Claims, 7 Drawing Sheets

(52) U.S. Cl.
CPC .............. *A61M 2025/0161* (2013.01); *A61M 2025/09008* (2013.01); *A61M 2025/09166* (2013.01); *A61M 2205/582* (2013.01); *A61M 2205/583* (2013.01)

(58) Field of Classification Search
CPC ......... A61M 2025/09008; A61M 2025/09166; A61M 2205/582; A61M 2205/583; A61M 25/0102; A61M 2025/018; A61M 25/01; A61M 25/09; A61M 25/09025; A61M 2025/09125; A61M 2025/09116
See application file for complete search history.

(56) References Cited

U.S. PATENT DOCUMENTS

| | | | | |
|---|---|---|---|---|
| 5,342,383 | A | * | 8/1994 | Thomas ............ A61B 17/12159 604/525 |
| 5,489,269 | A | * | 2/1996 | Aldrich .............. A61B 17/3415 604/95.04 |
| 5,489,271 | A | * | 2/1996 | Andersen ............ A61M 25/104 604/103.04 |
| 6,056,722 | A | * | 5/2000 | Jayaraman .......... A61M 25/104 604/528 |
| 6,496,561 | B1 | | 12/2002 | Meyer et al. |
| 2004/0097904 | A1 | | 5/2004 | Carrillo et al. |
| 2006/0015085 | A1 | * | 1/2006 | Bates ................. A61B 17/3478 604/508 |
| 2006/0036233 | A1 | * | 2/2006 | Boutillette ........ A61M 25/0169 604/528 |
| 2008/0082049 | A1 | | 4/2008 | Evans et al. |
| 2010/0094257 | A1 | * | 4/2010 | Stalker ................ A61M 25/104 604/524 |
| 2015/0051583 | A1 | * | 2/2015 | Horvath .............. A61M 25/007 604/523 |
| 2017/0050041 | A1 | * | 2/2017 | Cosman .................. A61N 1/36 |
| 2017/0113023 | A1 | | 2/2017 | Steingisser et al. |

FOREIGN PATENT DOCUMENTS

| | | |
|---|---|---|
| EP | 1 767 238 A1 | 3/2007 |
| JP | 2004-041790 A | 2/2004 |
| JP | 2010-80473 A | 4/2010 |
| WO | WO 1995/26213 | 10/1995 |
| WO | WO 1999/44687 | 9/1999 |
| WO | WO 2010/042882 | 9/1999 |
| WO | WO 2006/015323 A2 | 2/2006 |
| WO | WO 2012/104511 A1 | 8/2012 |
| WO | WO 2017/008918 A1 | 1/2017 |
| WO | WO 2017/031243 A1 | 2/2017 |
| WO | WO/2017/033039 A1 | 3/2017 |

* cited by examiner

USABLE-LENGTH-SELECTABLE CATHETER TO TREAT VASCULAR PATHOLOGIES

PRIORITY:

This application corresponds to the U.S. National phase of International Application No. PCT/EP2018/067102, filed Jun. 26, 2018, which, in turn, claims priority to European Patent Application No. 18.158627.2 filed Feb. 26, 2018, the contents of which are incorporated by reference herein in their entirety.

TECHNICAL FIELD

The current document is directed to catheters for the treatment of vascular pathologies and, in particular, to catheters with more than one usable-length configuration that are used for treating a variety of different vascular conditions.

BACKGROUND OF THE SUBJECT MATTER OF THE PRESENT DISCLOSURE

Angioplasty catheters have been developed to treat a variety of different manifestations of vascular disease within patients' veins and arteries that, when not treated, often lead to increasingly serious health conditions and complications, including ischemia, heart attacks, embolisms, and strokes. An angioplasty balloon catheter is generally inserted, along a previously inserted guide-wire, into a patient's blood vessel at a variety of different blood-vessel access points, including the femoral, subclavian, radial, and brachial arteries. The catheter is advanced along the guide-wire in order to position the inflatable portion of the angioplasty balloon catheter in or near a target region of the blood vessel. The balloon is then inflated in order to mechanically dilate and displace a blockage, lesion, or other problem within the target region. Currently available angioplasty catheters have fixed usable lengths, referring to the length portions of the instrument shaft that are inserted into a patient. As a result, a treatment provider generally selects dimensionally compatible pairs of guide-wires and catheters of anatomically adequate length in order to access a particular treatment site from a particular access point. However, in many procedures, a vessel is blocked at more than one point. In many cases, the treatment provider therefore needs to employ two or more angioplasty balloon catheters of two or more different lengths in order to reach and ameliorate the two or more blockages from the particular access point. Because angioplasty-balloon-catheter-based procedures involve prior insertion of the guide-wire, insertion and removal of multiple, different-length angioplasty balloon catheters may result in a variety of cascading complexities and problems, including a need to remove and reinsert different-length guide-wires, complexities associated with maintaining sterile protocols across multiple sub-procedures, increased procedure times, and potential for additional complications arising from additional procedural steps, including prolonged radiation exposure and contrast agent dosing. These challenges are further exacerbated by the medical device industry offering a vast variety of non-standardized product matrices that in turn result in increased hospital, warehouse and administration costs. For economic reasons, hospitals are obliged to be particular about the amount, types, sizes and configurations of products on stock. This frequently creates the sub-optimal situation that the treatment providers do not have the desired product sizes at their disposal when needed. Designers, developers, and treatment providers therefore continue to seek new and improved treatment equipment and associated methods for treating vascular pathologies.

A significant advance in dealing with the above issues was gaining the ability to exchange medical devices over a single indwelling guide-wire without requiring displacement of the wire in the process and loss of access to the site. This "over the wire" (OTW) exchange technique requires an extra-long guide-wire so that control over the wire would be maintained at all times during the procedure. To accomplish this, the portion of the wire extending out of the patient must be at least as long as the device itself so that a proximal portion of the wire could be secured at all times to maintain longitudinal positioning, typically by an assistant standing well behind the physician. For example, peripheral catheters that are used in a cross-over procedure, or in a radial approach, can easily exceed 150 cm or more length, requiring a guide-wire of more than 300 cm (e.g. 350 cm) to be long enough to remain in the vasculature during the exchange. Operating the catheter over such a long wire is cumbersome and always associated with a risk of making the catheter or the wire unsterile.

Although the "long wire" or OTW technique still remains a commonly method of exchanging devices, other techniques were developed which allowed for a much shorter guide-wire and more physician control over the wire. In general, there are three further types of wire-catheter systems:
1. multi-exchange (MX)
2. rapid exchange (RX) and
3. fixed wire (FW).

OTW, MX and RX catheters require the use of a guide-wire that is separate from the catheter while a FW catheter has an integral guide-wire. An OTW catheter comprises a guide-wire lumen that extends the entire length of the catheter. The guide-wire is disposed entirely within the catheter guide-wire lumen except for distal and proximal portions of the guide-wire, which extend beyond the distal and proximal ends of the catheter, respectively. An MX catheter is arranged such that it has an over-the-wire configuration while the catheter is within the patient's body, but the wire exits the side of the catheter through a zipper-like, longitudinal slit configuration at a location outside the body.

OTW and MX catheters provide a full length guide-wire lumen, whereas RX catheters provide a short guide-wire lumen only at or near the distal end. However, traditional OTW, MX and traditional RX catheters do suffer some shortcomings as described above. RX catheters were developed in attempt to simplify the procedure for exchanging wires and catheters. Catheters of this type are formed so that the guide-wire is located outside of the catheter except of a short guide-wire lumen that extends within only a comparatively short distal segment of the catheter. The RX catheters proximal exit port for the guide-wire is typically located about 5 cm to 30 cm proximal to the catheter's distal end. In use, the guide-wire is placed initially in the patient's vascular system. The distal segment of the RX catheter then is threaded onto the wire. The catheter can be advanced along the side the guide-wire with its distal segment sliding along the guide-wire. The RX catheter can be removed or exchanged with another RX catheter without the use of a very long exchange guide-wire and without requiring withdrawal of the initial placed guide-wire. However, the use of shorter guide-wires reduces the effective reach to treatment sites within the vasculature, severely limiting their scope of applicability.

MX catheters include a longitudinal slit extending most of the length of the catheter, from which a wire may be removed laterally, or "peeled off". At the distal end of the catheter is a short segment lacking the longitudinal slit, similar in nature to the short segment of the RX catheter. In use, a guide-wire may be inserted at the proximal end of the catheter, and advanced through the central lumen of the catheter, much like an OTW catheter. However, to remove the MX catheter, and not remove the wire, the proximal end of the wire (outside of the body) is laterally removed through the slit provided in the catheter wall. The MX procedure offers the benefit of an internal lumen delivery of the wire, similar to an OTW, but allows the user to avoid a double length guide-wire, similar to a RX catheter. However, the required "peeling-off" procedure is tedious as it requires holding onto the proximal end of the wire, and careful removal is required, as great care must be taken to ensure that the peeling off procedure does not damage the wire. The catheter is likely destroyed in the removal process and unfit for reinsertion.

In view of the above considerations it is still desirable to provide a catheter system which allows to select and adjust the usable length of the catheter during the medical procedure without having the limitations or drawbacks of the known OTW, MX, RX and FW systems. In particular, it would be desirable to provide a catheter system which combines the benefits of the known systems but which nevertheless allows an easy handling and in particular an easy selection of its usable length. Furthermore, it would be desirable to provide a catheter system that facilitates the usable length to be selected and changed during the medical procedure, without the requirement of removing and exchanging the catheter and/or the wire-guide.

Certain catheter systems are disclosed in the following prior art documents. However, none of these known catheter systems comprises the certain combination of features of the catheter system of the present invention and, therefore, none of the known systems solves the above described problems.

WO 2017/124059 is addressed to the technical problem of positioning a wire for advancement through a vessel wall. The systems and methods are intended for bypassing an occlusion or other barrier that may prevent advancement of a wire or tools through an endoluminal space. In particular, this document discloses a bypass catheter that includes two guide-wire ports and two deflection surfaces. The deflection surfaces are fixedly assigned to one for each of the two guide-wire ports and can be formed from a wall of the catheter. Accordingly, the position of either deflection surface is not movable relative to the assigned guide-wire port or shaft position.

US 2008/0082049 A1 is addressed to the technical problem of positioning a second guide-wire adjacent to a first guide-wire. In particular, this document discloses a guide-wire exchange catheter system comprising, among others, an exchange catheter, first and second guide-wires, and a securement element. The exchange catheter comprises a shaft having a lumen, and first and second segments, with guide-wire ports provided at the proximal end of each of the first and second segments. The securement element, which is movable relative to the catheter shaft, serves to secure the second guide-wire in position relative to the exchange catheter, at the most proximal guide-wire port located on the second segment.

US 2009/000574 A1 is addressed to the technical problem of releasably securing a guide-wire to an elongate medical device for introduction into a work site with the bodily lumen of a patient. In particular, this document discloses an elongate engagement member that comprises a wire stop member and an adjustable handle assembly, the engagement member having a distal end configured to frictionally engage the shaft of the guide-wire for adjusting the relative position of the distal end of the elongate engagement member relative to the elongate medical device.

US 2005/0113902 A1 is directed to a catheter delivery system having improved flexibility characteristics. In particular, this document discloses a rapid-exchange catheter system having an outer member, an inner member, a guide-wire exit port, a control handle, and a guide-wire. The control handle provides relative axial movement between the inner and outer member. A proximal portion of the inner member can be formed as a support mandrel, and a distal portion of the inner member may comprise a guide-wire receiving member that extends into the outer member.

The present inventors now found that the above problems can be solved by a catheter system which comprises a catheter having a catheter shaft with two or more guide-wire exit ports disposed laterally on the catheter shaft at different axial positions of the catheter shaft and a mandrel which is designed such that its tip can selectively be positioned relative to each one of the guide-wire exit ports such that the guide-wire can be guided through the selected guide-wire exit port.

SUMMARY OF THE SUBJECT MATTER OF THE PRESENT DISCLOSURE

The current document is directed to usable-length-selectable catheters and methods that employ usable-length-selectable catheters to treat malformations, constrictions, obstructions, lesions, and blockages within patients' blood vessels. The usable length of the shaft of a usable-length-selectable catheter, to which the current application is directed, can be selected over a set of lengths prior to and during medical procedures. In many implementations, usable-length selection is accompanied by relative-position indications, to the medical provider, of the extent of a usable length selection. The indications may include one or more of visual markings, haptic feedback, radio-opaque markings, and/or other types of indications. In many implementations, the usable-length-selection mechanism of the usable-length-selectable catheter is mechanically lockable following usable length selection.

The herein disclosed subject matter may in certain aspects be described by the following numbered clauses.

1. A catheter (110) extending along an axial direction from a proximal end to a distal catheter tip (111),
    the catheter comprising a distally disposed inflation balloon,
    a guide-wire lumen extending from a proximally disposed guide-wire port to the catheter tip (111),
    an inflation lumen extending from a proximally disposed inflation port to the inflation balloon,
    wherein at least two guide-wire exit ports are provided in communication with the guide-wire lumen and disposed laterally on a catheter shaft (115), the guide-wire exit ports disposed at different axial positions of the catheter.
    It will be appreciated that in particular the guide-wire exit ports are provided to provide a communication between the guide-wire lumen and an exterior of the catheter so as to enable a guide-wire to exit the catheter to an outside of the catheter, or to be inserted into the catheter from outside the catheter, respectively. A guide-wire exit port extends between the guide-wire lumen and a lateral outer surface of the catheter.

2. A catheter system comprising a catheter (110) and a mandrel,
   the catheter (110) extending along an axial direction from a proximal end to a distal catheter tip (111),
   the catheter comprising a distally disposed inflation balloon,
   a guide-wire lumen extending from a proximally disposed guide-wire port to the catheter tip (111),
   an inflation lumen extending from a proximally disposed inflation port to the inflation balloon,
   wherein at least one guide-wire exit port is provided in communication with the guide-wire lumen and disposed laterally on a catheter shaft (115),
   the mandrel comprising a mandrel shaft cross-sectionally being dimensioned and shaped so as to be received within the guide-wire lumen.
   It will be appreciated that in particular the guide-wire exit port is provided to provide a communication between the guide-wire lumen and an exterior of the catheter so as to enable a guide-wire to exit the catheter to an outside of the catheter, or to be inserted into the catheter form outside the catheter, respectively. A guide-wire exit port extends between the guide-wire lumen and a lateral outer surface of the catheter.

3. The catheter system according to the preceding clause, wherein at least two guide-wire exit ports are provided in communication with the guide-wire lumen and disposed laterally on a catheter shaft (115), the guide-wire exit ports disposed at different axial positions of the catheter.

4. The catheter system according to any preceding clause, wherein the mandrel comprises a handle (135) proximally attached to the mandrel shaft (132).

5. The catheter system according to any of the preceding clauses, wherein the mandrel comprises an axial stop portion sized and shaped to limit an insertion length of the mandrel into the guide-wire lumen and marking a proximal end of the mandrel shaft. The axial stop may for instance be a thickened portion. The handle and/or the axial stop prevent the mandrel from getting lost inside the guide-wire lumen and/or advancing with the distal tip of the mandrel distally beyond the distal tip of the catheter.

6. The catheter system according to the preceding clause, wherein the mandrel handle (135) is shaped to distally connect to a luer connector, and in particular to a female luer connector.

7. The catheter system according to any preceding clause, further comprising a lock-grip member (120), the lock grip member being shaped and configured to distally connect to the guide-wire port of the catheter and comprising an internal lumen configured to provide a proximal extension of the guide-wire lumen.

8. The catheter system according to the preceding clause, wherein the internal lumen of the lock-grip member is sized and shaped to receive the mandrel shaft.

9. The catheter system according to any preceding clause, wherein the lock grip member comprises a first connector and a second connector, the connectors being engaged with each other in an axial direction of the internal lumen, wherein the first connector comprises a free end sized and shaped to connect to the guide-wire port of the catheter and a free end of the second connector being sized and shaped to connect to a distal side of the mandrel handle.

10. The catheter system according to the preceding clause, wherein the first connector of the lock-grip member is provided at the free end with a male luer connector and/or the second connector of the lock-grip member is provided at its free end as a female luer connector.

11. The catheter system according to any preceding clause, wherein each of the first and second connectors of the lock-grip member comprises a front face, the front faces facing each other.

12. The catheter system according to the preceding clause, wherein an elastic cuff is provided between the two front faces, the cuff comprising a central orifice sized and shaped to receive the mandrel shaft therethrough when the cuff is in a neutral state, and wherein the cuff is adapted and configured to decrease the size of the central orifice when the cuff is subjected to a pressing force acting in the axial direction of the lock-grip member, or the internal lumen of the lock-grip member, respectively. The cuff may be adapted and configured so as to exert a clamping force on a mandrel shaft which is received within the orifice when an axial pressure force is exerted on the cuff.

13. The catheter system according to the preceding clause, wherein the orifice of the cuff is sized and shaped to provide a hemostatic sealing with the mandrel shaft when the mandrel shaft is received within the orifice and the cuff is in a neutral state.
   That implicitly means, when the cuff is axially pressed, it exerts a clamping force onto the mandrel shaft.

14. The catheter system according to the preceding clause, wherein the first and second connectors of the lock-grip member are threadedly engaged with each other.

15. The catheter system according to any preceding clause, wherein the cuff is received between the respective front faces of the first and second connectors of the lock-grip member and sized, shaped and configured such that an axial pressure force is exerted on the cuff in tightening the thread connection.

16. The catheter system according to any preceding clause, wherein the mandrel handle is configured to distally connect to at least one of the guide-wire lumen port and/or a distal end of a lock-grip member which is attached to the guide-wire port.

17. The catheter system according to any of the preceding clauses, wherein a mandrel reception port is provided by one of the proximal end of the guide-wire lumen and the proximal end attached to the guide-wire port, wherein the mandrel is axially dimensioned such that a distal tip (131) of the mandrel shaft may be advanced into the guide-wire lumen at least to a most distal lateral guide-wire exit port and at most to the tip (111) of the catheter.

18. The catheter system according to any preceding clause, wherein at least a distal tip (131) of the mandrel shaft is formed from a radiopaque material.

19. The catheter system according to any preceding clause, wherein a distal tip (131) of the mandrel shaft is shaped as a deflection tip.

20. The catheter system according to the preceding clause, wherein the distal tip of the mandrel shaft is at least one of beveled and/or rounded.

21. The catheter system according to any of the two preceding clauses, wherein the distal tip (131) of the mandrel shaft is shaped as a ramp.
22. The catheter system according to any of the three preceding clauses, wherein the distal tip (131) of the mandrel shaft comprises at least one of a spherical, a parabolic, a hyperbolic, and an ellipsoid geometry.
23. The catheter system according to any of the four preceding clauses, wherein the distal tip (131) of the mandrel shaft is either rotational symmetric of non-symmetric with respect to a longitudinal axis of the mandrel shaft.
24. The catheter system according to the preceding clause, wherein a most distal end of the distal tip (131) of the mandrel shaft is either centered or off-center of a cross-section of the mandrel shaft.
25. The catheter system of any preceding clause, wherein the mandrel shaft comprises cross sections wherein each cross section exhibits an at least essentially circular or non-circular shape.
26. The catheter system according to the preceding clause, wherein the cross sectional size and shape of the mandrel shaft is at least essentially constant along an entire axial extent of the mandrel shaft, except for a deflection tip.
27. The catheter system according to any preceding clause, wherein a mandrel lumen (1321) extends inside the mandrel from at least one of a distal or a proximal end of the mandrel, wherein
    in embodiments the mandrel lumen extends from a distal to a proximal end of the mandrel; and/or
    in embodiments the mandrel lumen runs centric inside the mandrel; and/or
    in embodiments the mandrel lumen exhibits a circular cross section; and/or
    in embodiments the mandrel lumen exhibits a constant cross section along its axial extent.
28. The catheter system according to any preceding clause, wherein at least one lateral port is provided in the mandrel shaft extending between the mandrel lumen and a lateral outer surface of the mandrel shaft.
29. The catheter system according to any preceding clause, wherein the mandrel shaft is provided as one of a rod, a hypotube and a braided tube, or a combination therefrom.
30. The catheter system according to any preceding clause, wherein at least one marking is provided on the mandrel shaft and located such that when the mandrel shaft is received within the guide-wire lumen and the marking is axially aligned with the mandrel reception port the mandrel shaft extends distally to a guide-wire exit port and in particular extends just to a guide-wire exit port, and wherein, in embodiments, the distal tip of the mandrel shaft is located underneath a guide-wire exit port.
31. The catheter system according to the preceding clause, wherein the catheter comprises at least two guide-wire exit ports, and a marking is provided on the mandrel shaft for at least one, and in particular each, lateral guide-wire exit port, and axially located on the mandrel shaft such that for each marking, when the mandrel shaft is received within the guide-wire lumen and the marking is axially aligned with the mandrel reception port, the mandrel shaft extends distally to a specific one of the guide-wire exit ports.
32. The catheter system according to the preceding clause, wherein each marking exhibits an individual and distinctive specific appearance, such as for instance color, and further markings are provided on the catheter shaft at the axial position of the lateral guide-wire exit ports, wherein each marking on the catheter shaft at a position of a specific lateral exit port exhibits an individual and distinctive specific appearance, for instance color,
    wherein markings on the catheter shaft and markings on the mandrel shaft exhibit corresponding appearances, wherein markings of corresponding appearance are axially located on the catheter shaft and the mandrel shaft, respectively, such that, when the mandrel shaft is received within the guide-wire lumen and a specific marking of the mandrel shaft is axially aligned with the mandrel reception port, the mandrel shaft extends distally to that one of the guide-wire exit ports the position of which is indicated by the marking on the catheter shaft with the corresponding appearance.
33. The catheter or catheter system according to any preceding clause, wherein the axial position of at least one lateral guide-wire exit port is indicated by a marking on the catheter shaft, and, wherein in particular the axial position of at least two lateral guide-wire exit ports are indicated by an individual and distinctive marking on the catheter shaft.
34. The catheter or catheter system according to any preceding clause, wherein two or more axially distant shaft markings are disposed on at least one of the catheter shaft and/or the mandrel shaft which provide visual, angiographic or haptic feedback to a treatment provider.
35. The catheter or catheter system according to any preceding clause, wherein the catheter comprises a catheter shaft and a manifold (119) disposed proximal of the catheter shaft, wherein the guide-wire lumen and the inflation lumen extend into the manifold, wherein the guide-wire port and the inflation port extend from the manifold, and at least one of said port may be shaped as a luer connector and in particular as a female luer connector.
36. The catheter or catheter system according to the preceding clause, wherein the guide-wire lumen extends straight through the manifold such that the guide-wire port extends axially.
37. The catheter or catheter system according to any of the two preceding clauses, wherein the inflation lumen is bent or cornered inside the manifold such that the inflation port is laterally displaced, in particular from the catheter shaft adjacent the manifold, to one side.
38. The catheter or catheter system according to the preceding clause, wherein at least one lateral guide-wire exit port is arranged on the same side of the catheter shaft, and, in particular, all lateral guide-wire exit ports are arranged on the same side of the catheter shaft as the side to which the inflation port is laterally displaced.
39. The catheter or catheter system according to any preceding clause, wherein a kink protection sleeve (118) is provided covering the catheter shaft adjacent the manifold.

It will be appreciated, that the mandrel is provided to selectively enable a guide-wire to exit the catheter at one or more guide-wire exit ports. When during selection of the guide-wire exit ports, the mandrel is adjustably inserted into the guide-wire lumen of the catheter shaft, the stiffness of the catheter shaft may be varied. Accordingly, in certain embodiments, the mandrel may be referred to as a stiffening mandrel.

The subject matter and features disclosed in the clauses above may be combined with each other. The skilled person will appreciate that the herein disclosed subject matter is not limited by the clauses above, but also comprises additional and supplemental disclosure and subject matter set forth below.

DETAILED DESCRIPTION

The current document is directed to a variety of different implementations of catheters with usable-length-selectable shafts that are used to treat vascular pathologies. The usable-length-selectable catheters facilitate the selection of the usable length that is applicable to render treatments of single target sites within blood vessels as well as procedures that involve treatment of multiple target sites. Because the usable shaft length of a usable-length-selectable catheter can be selected prior to and during a medical procedure, after the catheter has been initially inserted into a patient's blood vessel, the usable-length-selectable catheter provides for adjustment of initial non-optimal placements and/or guide-wire to catheter length mismatches, changes to which might otherwise involve removal of an initially inserted first catheter and/or guide-wire and reinsertion of a second catheter and/or guide-wire with a different length. The catheter thereby significantly simplifies treatments of multiple target sites within a blood vessel, since the usable length of the usable-length-selectable catheter can be changed, prior to and during a procedure, following treatment of a first target site, in order to reposition the catheter to treat a second target. Usable-length-selectable catheters may also reduce needed equipment inventories, since fewer different usable-length-selectable catheters are needed to span the potential range of usable lengths needed for accessing variably positioned treatment sites encountered in human anatomy. In addition, treatment providers may opt to select guide-wires that are shorter in length than the total usable length of the catheter, thereby providing significant handling improvement while still having the option to utilize the full total usable length of the instrument when needed. In the following discussion, examples of usable-length-selectable angioplasty balloon catheters are illustrated and described. Angioplasty balloon catheters are commonly employed in a variety of medical treatments. The usable-length-selectability discussed with reference to the various implementations of angioplasty balloon catheters can be applied to, and incorporated within, other types of catheters used for diagnostic and therapeutic procedures. While the description set forth below describes the catheter and catheter system in connection with its application to blood vessels, i.e. vascular applications, it is understood that the catheter and catheter system may in principle also be used in other body cavities, i.e. non-vascular applications, if deemed appropriate.

Catheter System

Figure 1:
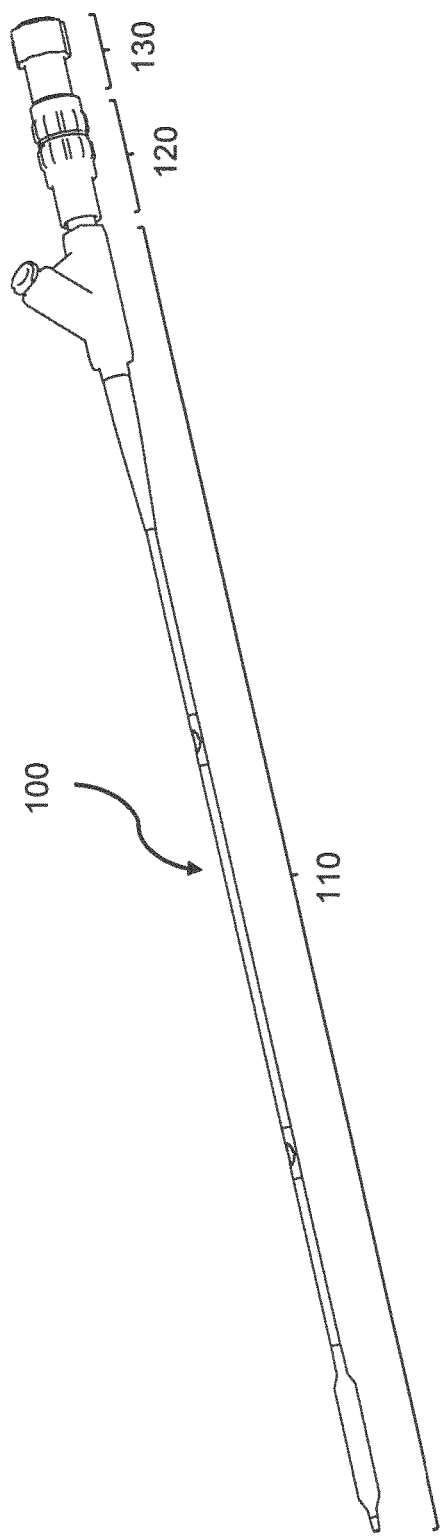
FIG. 1 illustrates a perspective view of the catheter system in an assembled state, as an embodiment.

The various components and features of the usable-length-selectable angioplasty balloon catheter system are next described with reference to FIGS. 1 through 7. FIG. 1 illustrates a perspective view of the catheter system of the present document in an assembled state, as an embodiment. In FIG. 1, the usable-length-selectable catheter system includes, from left to right, an angioplasty balloon catheter 110, a lock-grip 120, and a mandrel with handle 130. In an assembled state, the lock-grip 120 connects the catheter 110 to the mandrel with handle 130, as shown.

Figure 2:
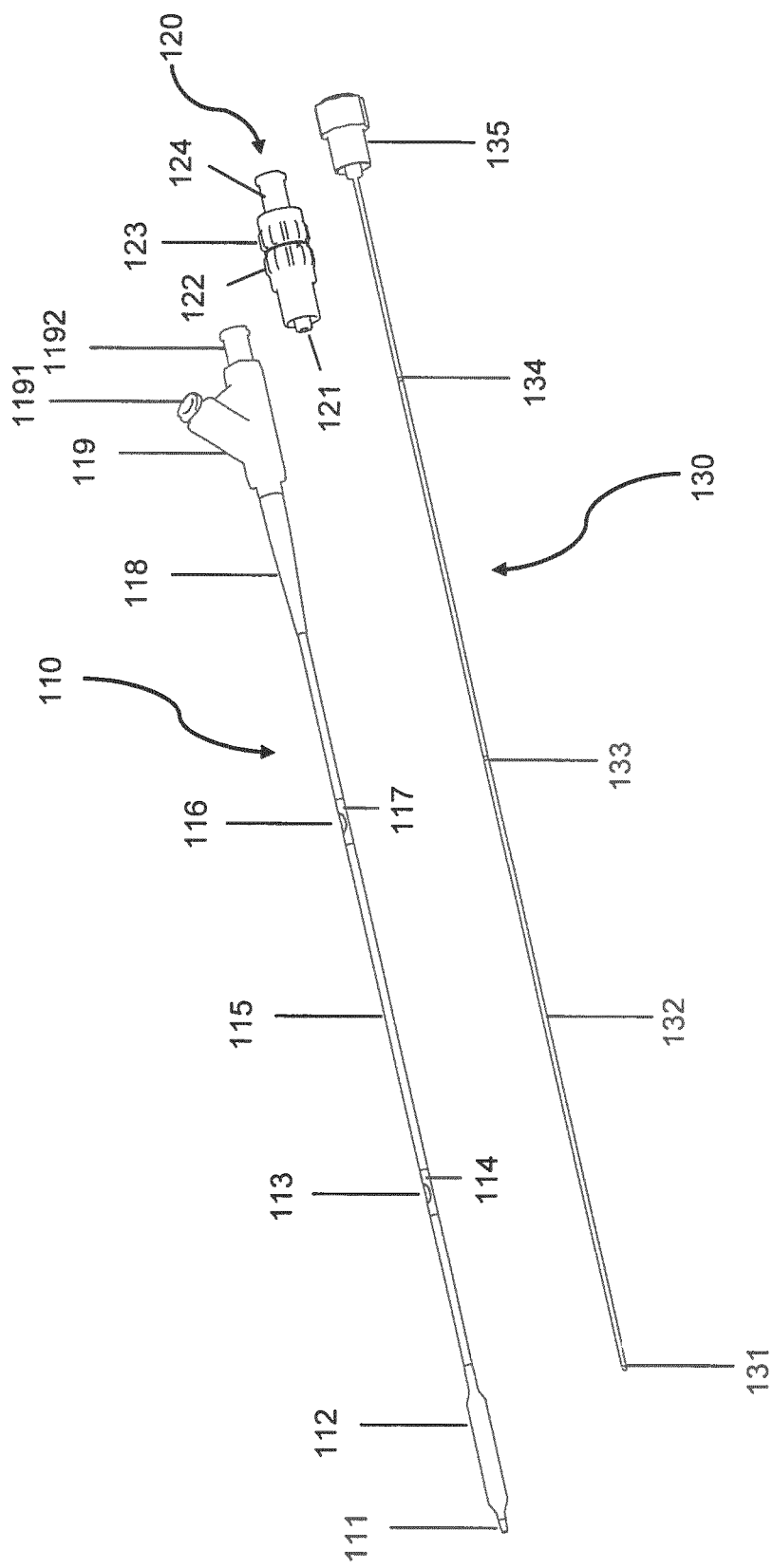
FIG. 2 illustrates a perspective diagram of the assembly components of the catheter system in a disassembled state, as several embodiments.

FIG. 2 is a perspective diagram illustrating the assembly components of the catheter system in a disassembled state, as several embodiments. In FIG. 2, the catheter 110 includes a manifold 119 with two ports: (1) an inflation port 1191; and (2) a guide-wire port 1192; with both ports extending from the manifold and shaped as female luer connectors. The manifold is mounted over a first end of a catheter shaft 115. A portion of the catheter shaft 115 close to the manifold is covered by a kink-protection sleeve 118. In the implementation shown in FIG. 2, the catheter shaft 115 further includes two internal lumens: (1) a first lumen intended as an inflation lumen connected to the inflation port 1191; and (2) a second lumen intended as a guide-wire lumen connected to the guide-wire port 1192.

The inflation lumen is connected to the inflation port 1191 and extends along the catheter shaft to an inflatable catheter balloon 112. Liquids and/or gases, including contrast-agent and saline formulations, air, and other such gases and/or liquids, may be transferred, under positive pressure inside the inflation lumen or at the inflation port, respectively, from the inflation port 1191 through the inflation lumen to the inflatable catheter balloon 112, resulting in inflation of the catheter balloon. The various liquids and/or gases are transferred, under negative pressure inside the inflation lumen or at the inflation port, respectively, from the inflated catheter balloon 112 back through the inflation lumen and out through the inflation port 1191, deflating the catheter balloon. "Positive pressure" and "negative pressure" designate pressures which are larger than, or smaller than, respectively, the pressure around balloon 112.

The guide-wire lumen extends from the guide-wire port 1192 to the tip 111 of the catheter shaft. This particular guide-wire lumen configuration enables over-the-wire (OTW) operation of the catheter, meaning that the usable-length-selectable catheter can be slidably mounted onto a guide-wire and translated in either direction along an entire indwelling portion of the guide-wire lumen during insertion of a portion of the shaft into a patient's blood vessel. The OTW configuration therefore may utilize up to the complete usable length of the catheter, which spans from the tip or distal end of the kink-protection sleeve 118 to the tip 111 of the catheter. The exemplarily shown catheter shaft 115 further includes at least two guide-wire exit ports: (1) a first guide-wire exit port 113; and (2) a second guide-wire exit port 116; both of said exit ports located between a second end of the catheter shaft 115 and the tip of the kink-protection sleeve 118. The guide-wire exit ports 113, 116 are formed within a lateral surface of the catheter shaft and provide lateral access to the guide-wire lumen from a side of the catheter shaft opposite to the inflation lumen. The guide-wire lumen may be considered to comprise a first portion extending from the tip 111 to first guide-wire exit port 113; a second portion extending from first guide-wire exit port 113 to the second guide-wire exit port 116; and a third portion extending from second guide-wire exit port 116 to guide-wire port 1192. The guide-wire may thus extend inside the guide-wire lumen from the tip 111 of the catheter within the first portion of the guide-wire lumen and along a first shaft axis, from distal to proximal, to guide-wire exit port 113; or within the combined first and second portions of the guide-wire lumen, along a first and second portion of the shaft axis, to guide-wire exit port 116; or within the combined first, second and third portions of the guide-wire lumen along the first, second and third portions of the shaft axis, to guide-wire port 1192. In the implementation shown in FIG. 2, the shaft 115 may further exhibit locally confined shaft sections 114, 117, each placed symmetrically over an axial region that coincides with the respective axial location of the guide-wire exit ports 113, 116. These shaft sections 114, 117 include additional layers formed over, within or beneath the shaft surface to provide (a) visually, haptically or angiographically distinct appearance from the shaft and (b) structural reinforcement at the axial regions of the guide-wire exit ports 113, 116. The particular guide-wire lumen configurations embodied by guide-wire exit ports 113, 116 enable rapid-exchange (RX) operation of the catheter, meaning that the usable-length-selectable catheter can be slidably mounted onto a guide-wire and translated in either direction such that the guide-wire passes along a first or second portion of the guide-wire lumen during insertion of a portion of the shaft into a patient's blood vessel. For clarification, in RX operation the guide-wire may be partially exposed alongside the catheter shaft, when located within the indwelling portion, whereas in OTW operation, the guide-wire is fully shielded by the catheter shaft, when located within the indwelling portion. The RX configuration utilizes an individually selectable portion of the usable length of the catheter spanning from the tip 111 of the catheter shaft to one of: (1) guide-wire exit port 113; or (2) guide-wire exit port 116. FIGS. 7A-B provide additional details on the possible modes of guide-wire operation.

The inflation lumen and the guide-wire lumen are completely separate from one another, so that there is no possibility for leakage of the liquids and/or gases transported by the inflation lumen into the guide-wire lumen or for leakage of fluids within the guide-wire lumen into the inflation lumen. The inflation lumen and the guide-wire lumen laterally extend in parallel to each other (side-by-side). The guide-wire exit ports 113, 116 are provided on an opposite side of the wall delimiting the guide-wire lumen from the inflation lumen.

In the implementation shown in FIG. 2, a lock-grip 120 includes a male luer connector 121, a first gripping surface 122, a second gripping surface 123, and a female luer connector 124. An internal lumen of the lock-grip extends from the connector 121 to the connector 124 and is configured to form a proximal appendix of the guide-wire lumen when the lock-grip is attached to the catheter. In assembled state, the male luer connector 121 of the lock-grip 120 couples to the female luer of the guide-wire port 1192 of the catheter 110. A mandrel 130 comprising a shaft 132 and a handle 135 proximally attached to the shaft is provided. Shaft 132 is configured shaped and dimensioned to be inserted into the proximal, female, luer 124 and to be received within the internal lumen of the lock-grip and the guide-wire lumen. A deformable cuff, having a central orifice with an inner cross-sectional dimension, is located within the lock-grip, and forms part of the internal surface of its inner lumen (not shown). When the two gripping surfaces 122, 123 of the lock-grip are mechanically engaged, the cuff deforms such that the inner cross-sectional dimension of the inner lumen decreases. Upon disengagement of the two gripping surfaces, the cuff assumes its original dimensions such that the full inner cross-sectional dimension of the inner lumen is restored. When the mandrel is inserted through the lock-grip, the mechanical engagement of the lock-grip yields a gripping force that arrests the mandrel in position.

In the implementation shown in FIG. 2, the mandrel 130 includes a tip 131, shaped as a deflection surface, a shaft 132, two or more shaft markings 133, 134, and a handle 135, shaped as a male luer. In assembled state, the smaller-outer-diameter shaft 132 of the mandrel 130 slides through the inner lumen of the lock-grip 120 into the larger-inner-diameter guide-wire lumen of the catheter 110. The mandrel is cross-sectionally sized such, that it is fittingly received within the orifice of the cuff, and, without significant sliding movement restriction, when the cuff is in a neutral, non-deformed state. Thus, when the mandrel shaft 132 passes through the inner lumen of the lock-grip in disengaged state, the cuff seals around the surface of the mandrel shaft 132, facilitating hemostatic sealing. Upon engaging the lock-grip, the position of the mandrel with handle locks in an axial direction relative to the position of the shaft 115 of the catheter 110. The lock-grip 120 thus provides hemostatic sealing and insertion length locking for the mandrel with handle 130, when the lock-grip 120 is attached to the catheter 110. In the implementation shown in FIG. 2, the handle 135, shaped as a male luer, is an optional component fixedly attached to the shaft 132 that (a) facilitates improved mandrel handling during operation and (b) reversibly attaches to the female luer 124 of the lock-grip 120 during storage of the catheter system. In other implementations, the mandrel shaft may include a lumen, formed from a hollow-bore hypotube, and/or reinforced or braided tubing, and/or a combination formed therefrom. In addition, the mandrel handle shaped as male luer may include a port connected to the lumen of the mandrel shaft.

Dimensions

Figure 3:
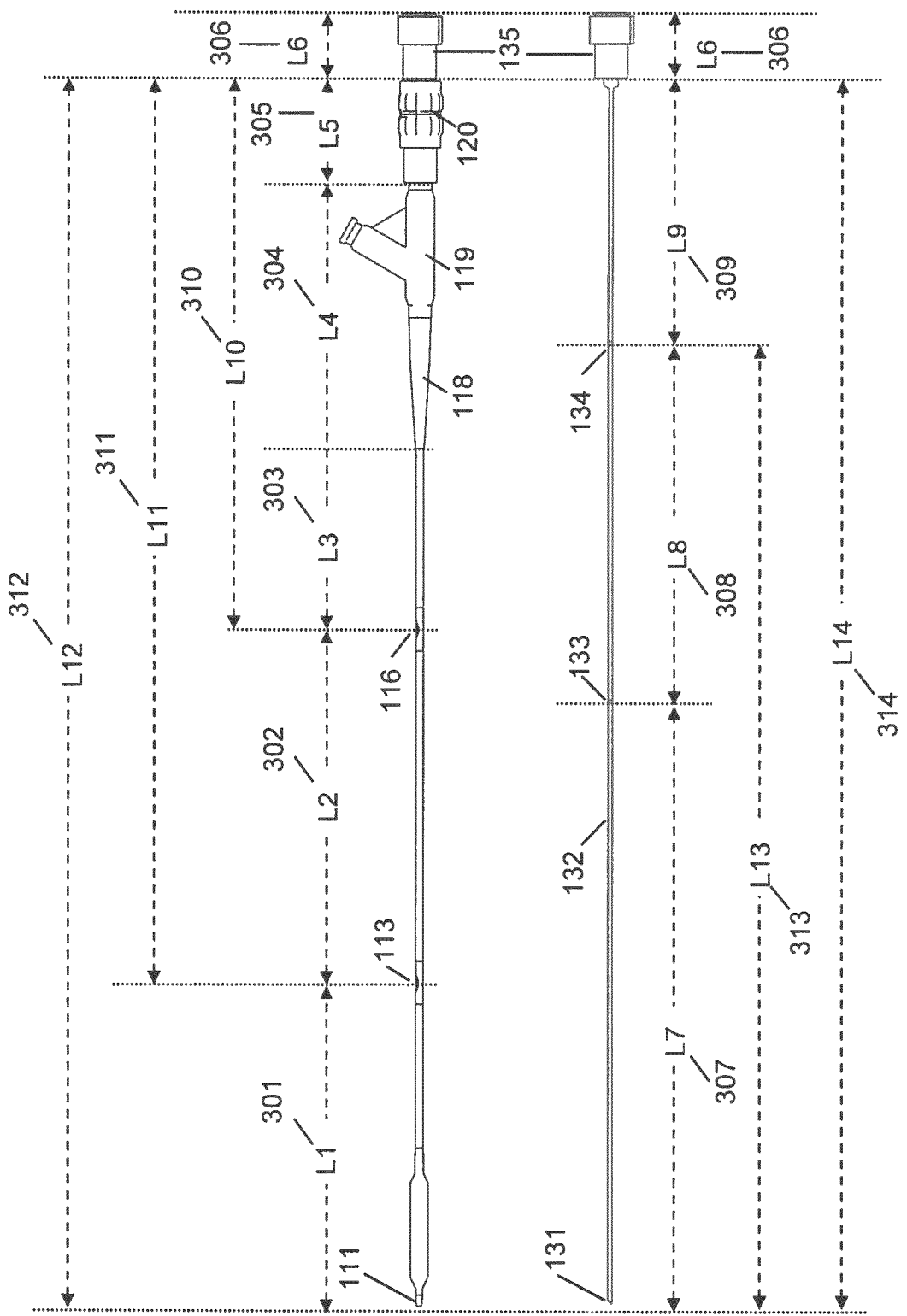
FIG. 3 illustrates a cross-lateral view of the dimensional relationships of the components of the catheter system, as several embodiments.

FIG. 3 illustrates a cross-lateral view of the dimensional relationships of the components of the catheter system, as several embodiments. The total length of the catheter system is given by the added lengths L1-L6 (301-306), that include the length L1 (301), from catheter tip 111 to first guide-wire exit port 113, length L2 (302) from first guide-wire exit port 113 to second guide-wire exit port 116, length L3 (303) from second guide-wire exit port 116 to distal end of the kink-protecting sleeve 118, length L4 (304) from distal end of the kink-protecting sleeve 118 to the proximal end of the manifold 119, length L5 from the proximal to the distal end of the lock-grip 120, and length L6 from the proximal to the distal end of the mandrel handle 135. The total length of the mandrel 130 is given by the added lengths of L7-L9 and L6 (307, 308, 309, 306), that include the length L7 (307), from mandrel tip 131 to first marker 133, the length L8 (308) from first marker 133 to second marker 134, the length L9 (309) from second marker 134 to the proximal end of the mandrel handle 135, and the length L6 (306) from proximal to distal end of the mandrel handle 135. In the implementation shown in FIG. 3, the length L14 (314) of the mandrel shaft 132 (that includes the added lengths L7, L8, L9) is equal to or smaller than the total length of the angioplasty balloon catheter L12 (312), that includes the added lengths L1 to L4, plus the length L5 of the lock-grip. The length L11 (311), that includes the added lengths L2, L3, L4, L5, is equal to the length L13 that includes the lengths L7, L8. The length L10, that includes the added lengths L3, L4, L5, is equal to the length L7. Finally, the length distance L2 between the two guide-wire exit ports 113, 116 is equal to the distance L8 from first marker 133 to second marker 134. In the implementation shown in FIG. 3, the length L1 equals 50 cm, L2 equals 30 cm, L3 equals 55 cm, L4 equals about 8-10 cm, L5 about 2-4 cm, and L6 about 1-2 cm. The dimensions may include additional tolerances to account for luer coupling depths, and an arbitrary exposition length to visually expose the marker(s) to a treatment provider.

Usable-Length-Selection

FIGS. 4A-E illustrate cross-lateral views representing five consecutive configurational stages A-E for selecting the usable length of the catheter system. In FIG. 4A, the catheter system is shown in fully assembled state: The lock-grip 120 is attached to the catheter 110. The mandrel with handle 135 is fully inserted through the lock-grip into the catheter shaft 115, such that the openings of both guide-wire exit ports 113 and 116 are axially covered by the mandrel shaft. In this configuration, the lock-grip is mechanically disengaged, i.e. un-locked, and the handle 135 of the mandrel coupled to the lock-grip. Through rotation of the handle 135, indicated by a dashed circular arrow, the mandrel 130 is uncoupled from the lock-grip such that the mandrel with handle is enabled to slidably move within the guide-wire lumen of the catheter shaft 115 of the catheter, facilitating either position adjustment within the guide-wire lumen or removal therefrom. In other implementations, the lock-grip 120 reversibly mechanically engages the mandrel in the absence of a handle 135.

In FIG. 4B, the lock-grip 120 mechanically engages, i.e. locks, the position of the shaft 132 of the mandrel 130 relative to the shaft 115 of the catheter 110. Through rotation of the second gripping surface 123 of the lock-grip 110, indicated by a dashed circular arrow, the lock-grip mechanically disengages the mandrel shaft 132. In this state, the treatment provider may pull the mandrel proximally to expose the mandrel shaft 132 with the two or more shaft markers 133, 134. When displacing the mandrel in this manner, the treatment provider can opt to: (1) align the position of the first shaft marker 133 with the proximal end of the lock-grip (FIG. 4C); (2) align the position of the second shaft marker 134 with the proximal end of the lock-grip (FIG. 4D); and/or (3) remove the mandrel entirely (FIG. 4E).

Hence, in FIG. 4C the position of the second shaft marker 134 is adjusted such that its position aligns with the proximal end of the lock-grip (female luer connector). The mandrel position relative to the catheter shaft is locked through counter-rotation of the second gripping surface 123 of the lock-grip 110, indicated by a dashed circular arrow. In this position, the deflection surface of the mandrel tip aligns underneath the first guide-wire exit port 113. Further, a proximal edge of the deflection surface aligns with a proximal edge of guide-wire exit port. This feature is illustrated in greater detail in FIG. 5. "Underneath" shall in this respect not be construed to mean "below" in an absolute geometric sense. In this first usable length configuration, a selectable portion of the guide-wire lumen extends from the tip 111 of the catheter 110 to the first guide-wire exit port 113, defining a first usable length UL1 (451). Upon passing the instrument over a guide-wire, beginning from the catheter tip 111, the guide-wire exits at a designated first guide-wire exit port 113. In the exemplary implementation of FIG. 4C, the guide-wire exit port 113 is placed at a distance of, for instance, 50 cm from the catheter tip 111, thereby providing an exemplary first usable length of 50 cm.

In FIG. 4D, the position of the first shaft marker 133 is adjusted such that its position aligns with the proximal end of the lock-grip, placing the deflection surface of the mandrel tip underneath the second guide-wire exit port 116. In this second usable length configuration, the selectable portion of the guide-wire lumen extends from the tip 111 of the catheter 110 to the second guide-wire exit port 116, defining a second usable length UL2 (452). Upon passing the instrument over a guide-wire, beginning from the catheter tip 111, the guide-wire exits at a designated second guide-wire exit port 116. In the implementation of FIG. 4D, the guide-wire exit port 116 is placed at a distance of, for instance, 80 cm from the catheter tip 111, thereby providing an exemplary second usable length of 80 cm.

It will be appreciated that deflection tip 131 of the mandrel assists in deflecting the guide-wire out of the respective exit port when the guide-wire is inserted into the guide-wire lumen from the tip of the catheter, or when the catheter is pushed over the guide-wire, respectively, so as to reliably avoid deadlock of the guide-wire with the mandrel, as outlined below.

Figure 4:
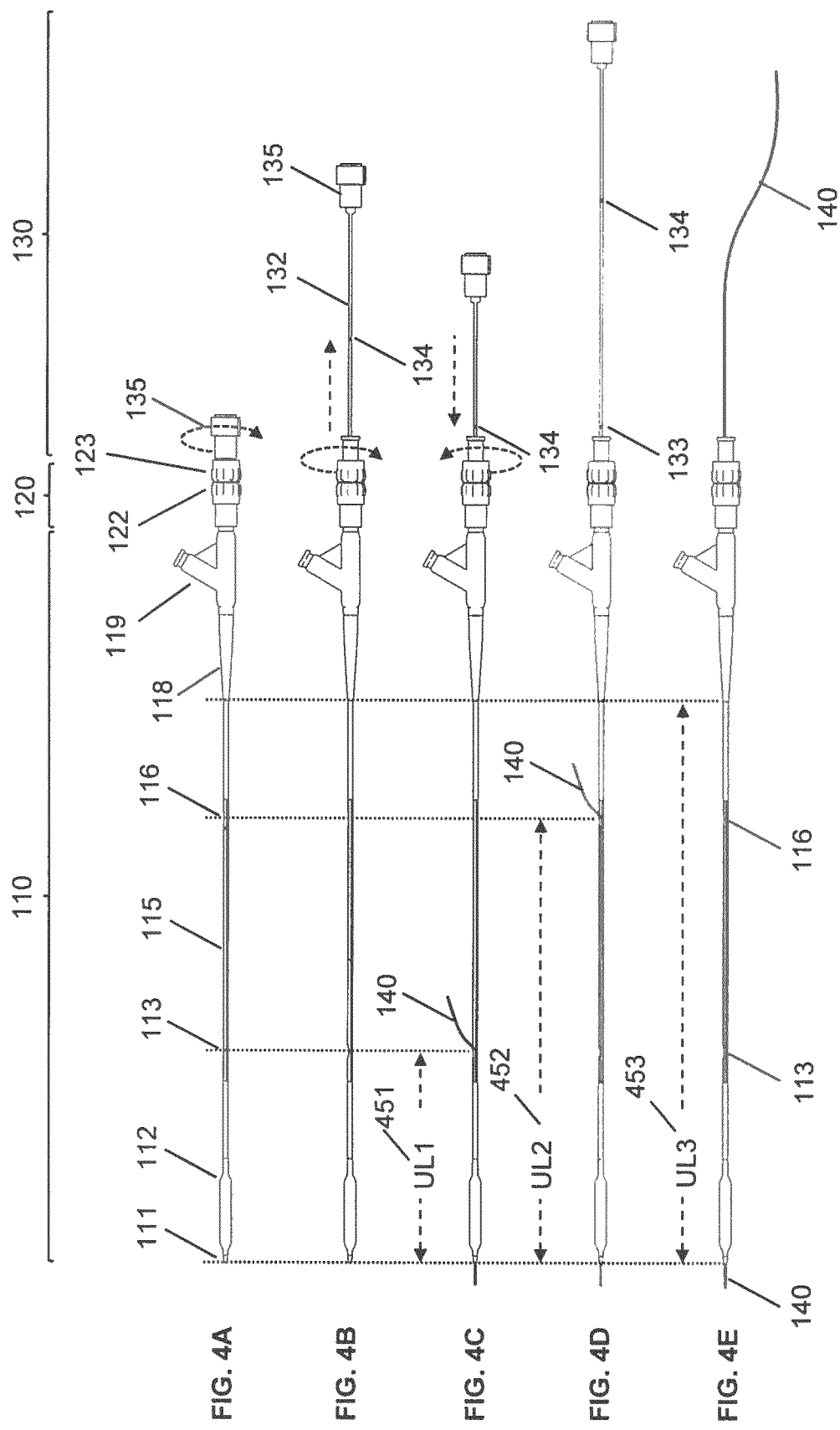
FIGS. 4 A-E illustrate cross-lateral views representing five consecutive configurational stages A-E for selecting the usable length of the catheter system, as several embodiments.

In other implementations of FIG. 4, shaft markings 133, 134 may be color-indicated to the treatment provider, and the shaft section 114 of the first guide-wire exit port 113 may exhibit the same or corresponding color as the second marker band 134, and section 117 of the second guide-wire exit port 116 may exhibit the same or corresponding color as the first marker band 133.

In FIG. 4E, the mandrel 130 is removed from the catheter 110 and lock-grip 120 entirely. In this third usable length configuration, the guide-wire lumen extends from the tip 111 of the catheter 110 to the guide-wire port 1192.

The usable length in turn spans from the tip 111 of the catheter to the tip of the kink-protection sleeve 118, defining a third usable length UL3 (453). Upon passing the instrument over a guide-wire, beginning from the catheter tip 111, the guide-wire exits at a designated third guide-wire port 1192. In the implementation of FIG. 4E, the tip of the kink-protection sleeve 118 is placed at a distance of, for instance, 135 cm from the catheter tip, thereby providing a third, or total, exemplary usable length of 135 cm. In other implementations, the described sets of usable-lengths of the usable-length-selectable catheter may have different numbers, sizes, configurations, shapes, and constructions.

Guide-Wire Deflection Mechanism

Figure 5:
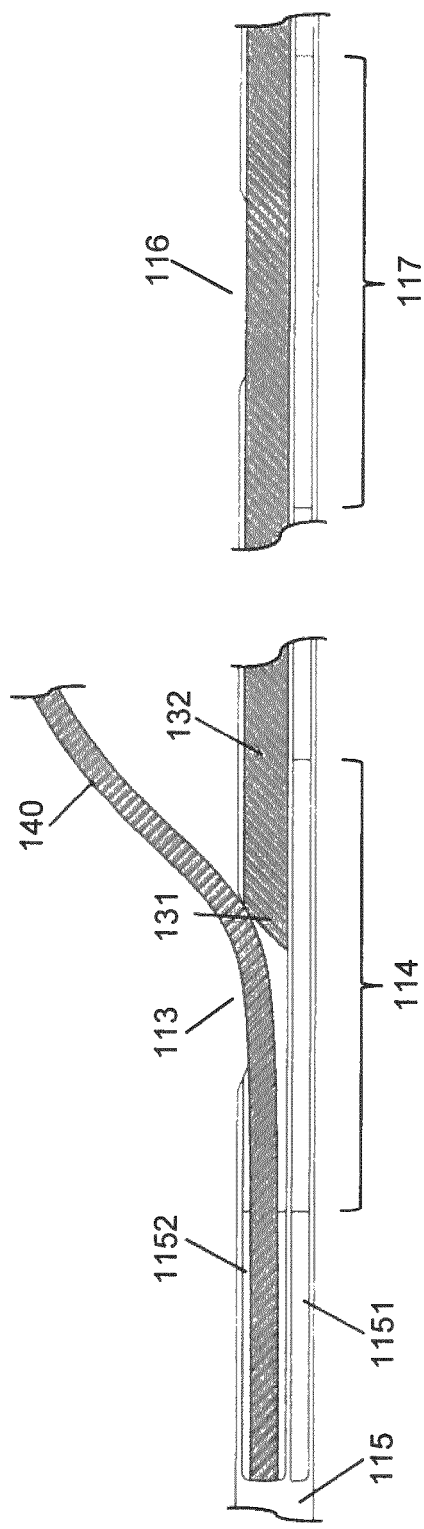
FIG. 5 illustrates a cross-sectional view of a guide-wire deflection mechanism enabling usable length selection, as one embodiment.

FIG. 5 illustrates a cross-lateral view of the guide-wire deflection mechanism enabling usable length selection, as one embodiment. In FIG. 5 the catheter shaft 115 is shown in dual lumen configuration, represented by: (1) inflation lumen 1151; and (2) guide-wire lumen 1152. The guide-wire lumen is positioned adjacent the inflation lumen. The shaft 115 includes two guide-wire exit ports 113, 116 that connect to the guide-wire lumen 1152. The mandrel shaft 132 is shown partially inserted in the guide-wire lumen. The mandrel tip 131, shaped as a beveled deflection surface, is positioned underneath the first guide-wire exit port 113, located in shaft section 114. The opening of the second guide-wire exit port 116, located in shaft section 117, is shielded by the mandrel shaft 132. When a guide-wire 140 impinges on the deflection surface of the mandrel tip 131, the guide-wire tip, or end, is deflected away from the deflection surface, in opposite direction to the inflation lumen, and through the first guide-wire exit port 113. In other implementations, the deflection tip may be, for instance, rounded, spherical or conical, and may be symmetric or asymmetric with respect to a longitudinal axis of the mandrel shaft. While non-symmetric geometries may yield benefits in providing a well-defined direction of guide-wire deflection, symmetric tip designs may yield the benefit of easier use.

Figure 6:
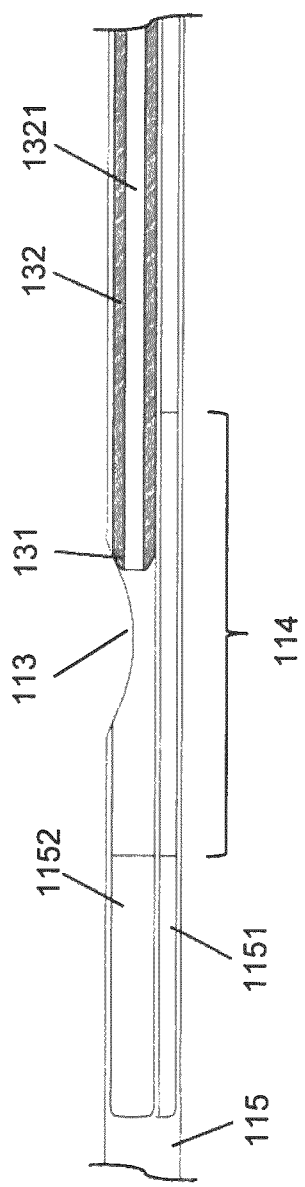
FIG. 6 illustrates a cross-sectional view of a mandrel with an injection lumen enabling the injection or aspiration of various diagnostic, therapeutic and/or body liquids, as one embodiment.

In the implementation shown in FIG. 6, the catheter shaft 115 is shown in dual lumen configuration, represented by: (1) inflation lumen 1151; and (2) guide-wire lumen 1152. The guide-wire lumen is positioned adjacent the inflation lumen. The shaft 115 includes two guide-wire exit ports, whereof only exit port 113 is shown, that connect to the guide-wire lumen 1152. The mandrel shaft 132 is partially inserted in the guide-wire lumen, with the mandrel tip 131 positioned underneath the first guide-wire exit port 113. The mandrel tip 131 is shaped as a rounded deflection surface, and formed from a radiopaque material. Forming the deflection surface as a symmetric, for instance semispherical or otherwise rounded, tip alleviates the potential problem of orienting a tapered deflection surface within an inner guide-wire lumen of a shaft relative to a guide-wire exit port.

In the implementation shown in FIG. 6, the mandrel shaft further includes an injection lumen 1321, extending from the deflection surface of the mandrel tip 131 to a second end of the mandrel shaft 132. The mandrel extends to a proximal end of the mandrel handle. When the mandrel tip 131 is positioned underneath one of the two or more guide-wire exit ports 113, 116, the injection lumen 1321 within the mandrel shaft 132 enables the injection or aspiration of various diagnostic, therapeutic and/or body liquids, from a proximal end of the mandrel handle, through the mandrel lumen 1321 to either one of the two or more guide-wire exit ports 113, 116. In the related implementation shown in FIG. 8, the mandrel may instead contain a lumen that exits through a lateral shaft surface portion rather than through the tip. In a cross-lateral depiction, the opening section may then assume a crescent shape that extends sideways into the lumen of the mandrel shaft.

In the implementation shown in FIG. 6, the injection lumen present in the mandrel shaft has an inner diameter of 0.3556 mm, or 0.014 inch. For deflection of a guide-wire, the corresponding guide-wire preferably may have an outer diameter of either 0.4572 mm, or 0.018 inch, or larger. Such construction prevents the larger-diameter guide-wire from inadvertently entering the injection lumen when impinging onto the deflection surface from a proximal direction. Alternatively, the injection lumen can be utilized to pass a 0.014 inch guide-wire in distal direction, from a proximal end of the mandrel handle through the injection lumen 1321 that exits at the mandrel tip shaped as a rounded deflection surface, and through a first or second portion of the catheter guide-wire lumen 1152, to the tip of the catheter shaft 115. Using the injection lumen as an alternate guide-wire lumen therefore facilitates a convenient exchange of guide-wires while leaving both the catheter and the inserted mandrel in place. Further still, because the mandrel with injection lumen may stay in place without obstructing the passage of smaller-diameter guide-wires, the mandrel can be effectively utilized for varying the degree of stiffness of the catheter shaft.

Figure 8:
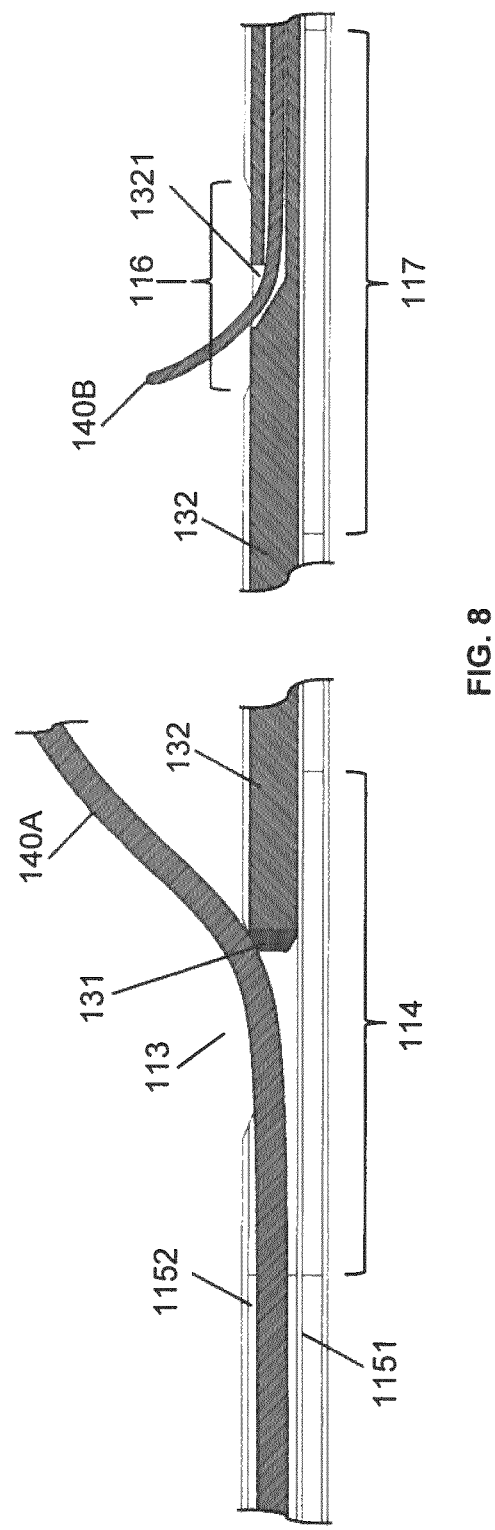
FIG. 8 illustrates a cross-sectional view of a mandrel with a lateral pass-through guide-wire and/ or injection lumen enabling usable length selection, side branch access, and/or injection or aspiration of various diagnostic, therapeutic and/or body liquids, as several embodiments.

FIG. 8 illustrates a cross-lateral view of a mandrel with a lateral pass-through guide-wire and/ or injection lumen enabling usable length selection, side branch access, and/or injection or aspiration of various diagnostic, therapeutic and/or body liquids, as several embodiments. When the injection lumen 1321 is configured to exit not directly through the deflection surface of the mandrel tip 131, but laterally through a surface of the mandrel shaft 132, a 0.014 inch guide-wire 140B, passed distally, is deflected sideways to exit through one or more of the guide-wire exit ports 113, 116. Such described configuration enables either one of (1) deflection of a proximally passed guide-wire 140A; and/or (2) deflection of a distally passed guide-wire 140B. The treatment provider can therefore utilize the system to (1) pass a first guide-wire 140A of 0.035 inch through the first guide-wire exit port 113; and, at substantially the same time, (2) pass a second guide-wire 140B of 0.014 inch, from a port at the mandrel handle, through the second guide-wire exit port 116. Using the injection lumen in this manner enables the convenient access and probing of side branch vessels. The treatment provider may beneficially utilize such configuration in preparation of a second, side-branch treatment site while the catheter is still positioned at a first treatment site. In other implementations, the catheter system may include a set of mandrels with mandrel tips including (1) injection lumen with straight pass-through; and (2) injection lumen with lateral pass-through to grant a maximum degree of versatility to the treatment provider.

As is readily apparent by comparing the at least three guide-wire configurations described in FIGS. 4 C-E, the guide-wire configurability enabled by the select positioning and length-locking of the mandrel tip, shaped as deflection surface and as part of the mandrel within the guide-wire lumen of the catheter shaft enables a treatment provider to choose from two possible modes of operation during use: (1) RX operation; and (2) OTW operation. The inherent guide-wire configurability of the catheter system enables the treatment provider to select from the at least three usable lengths (1) UL1; (2) UL2; and (3) UL3, embodied by the three or more guide-wire lumen configurations described above. In addition, the length-lockable insertion of the mandrel into the catheter shaft, facilitated through the locking-mechanism of the lock-grip, enables the treatment provider to variably adjust the flexibility of the catheter shaft length-wise, thereby enhancing maneuverability and push-ability of the catheter system. In other implementations, based on the choices of mandrel material, and depending on the degree of mandrel insertion relative to the catheter shaft, varying degrees of shaft flexibility and/or stiffening properties of the catheter system may be obtained. In yet other implementations, the mandrel enables the injection or aspiration of various diagnostic, therapeutic and/or body liquids, and, at substantially the same time, may serve as an alternate guide-wire lumen that facilitates the convenient exchange of guide-wires while leaving both the catheter and the inserted mandrel in place.

Variable-Usable-Length Selection

Figure 7:
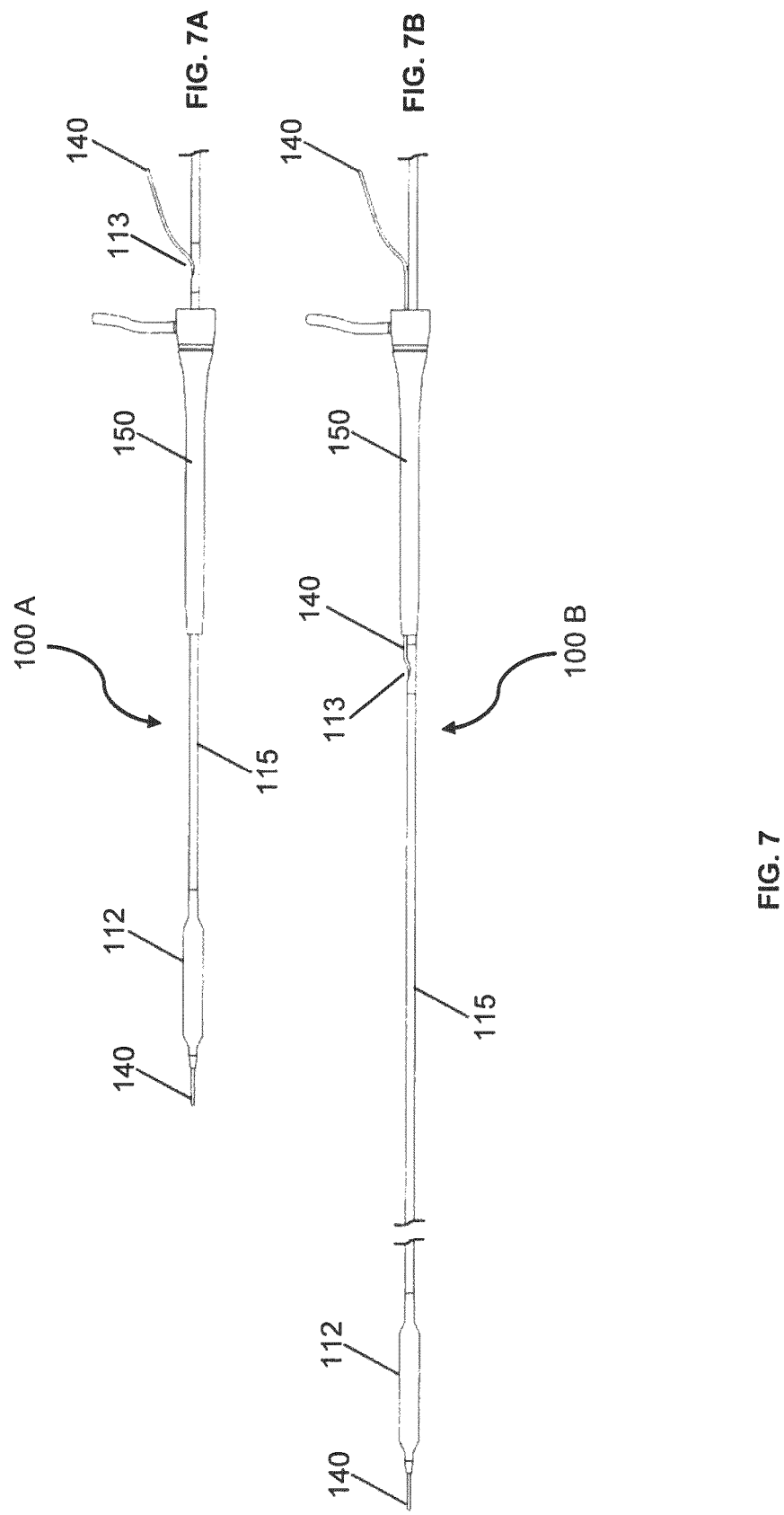
FIG. 7 A-B illustrate two cross-lateral views of the catheter system arranged in an over-the-wire (OTW) configuration (FIG. 7A) and in a rapid-exchange (RX) configuration (FIG. 7B), as several embodiments.

FIG. 7 A-B illustrate two cross-lateral views of the catheter system arranged in an OTW configuration (FIG. 7A) and in a RX configuration (FIG. 7B). In FIGS. 7 A-B, the catheter systems 100 A and 100 B include a balloon 112, a shaft 115 and a first guide-wire exit port 113. Both systems are passed over a guide-wire 140 and through an introducer sheath 150. The distance from catheter tip to the proximal end of the introducer sheath is equivalent to the usable length or indwelling portion.

In the OTW implementation shown in FIG. 7A, the introducer sheath 150 is positioned distal to the guide-wire exit port 113. Starting from the distal tip of the balloon 112, the guide-wire 140 passes through the inner guide-wire lumen of the catheter shaft 115 and exits through the guide-wire exit port 113, positioned proximal to the proximal end of the introducer 150. In this OTW configuration, the guide-wire passes through the guide-wire lumen of the catheter shaft, along the entire length of the indwelling catheter portion. The usable length in turn is equivalent to the distance from catheter tip to the proximal end of the introducer sheath, aligning with the position of the guide-wire exit port 113. By further distal propagation of the catheter instrument 100 A (through the introducer sheath 150), the treatment provider can conveniently switch from an OTW configuration to the RX configuration depicted in FIG. 7B, thereby further extending the usable length portion of the catheter:

In the implementation shown in FIG. 7B, the introducer sheath 150 is positioned proximal to the guide-wire exit port 113. Starting from the distal tip of the balloon 112, the guide-wire 140 passes through the inner guide-wire lumen of the catheter shaft 115 and exits through the guide-wire exit port 113, positioned distal to the distal end of the introducer 150. The guide-wire then continues to pass in parallel to the catheter shaft 115 and through the lumen of the introducer sheath 150, exiting at its proximal end. In this RX configuration, the guide-wire passes through a first or second portion of the guide-wire lumen of the catheter shaft, after which it proceeds in parallel to the shaft, through the lumen of the introducer sheath 150, along the remainder of the indwelling catheter portion. In this particular RX configuration, the usable length can be extended to cover the distance from catheter tip to the proximal end of the introducer sheath beyond the position of the guide-wire exit port 113. Enabling the treatment provider to switch from OTW to RX configuration in this manner carries the benefit, that the usable length of the catheter system becomes extendable without having to exchange the guide-wire or replace the catheter. In addition, the first selected guide-wire exit port may remain selected without having to switch to a second or a third guide-wire exit port. Finally, the treatment provider may variably adjust the usable length between the position of the (1) first and the second guide-wire exit port; and (2) the second guide-wire exit port and the tip of the kink-protection sleeve.

Accordingly, the set of usable lengths that can be adopted by the usable-length-selectable angioplasty balloon catheter arises from the two or more guide-wire exit ports located on the catheter shaft, and the guide-wire port located at the catheter manifold. Selective positioning of the mandrel within the guide-wire lumen of the catheter shaft, indicated to the treatment provider by the two or more shaft markings, followed by length-wise locking of the mandrel shaft, or removal of the mandrel from the guide-wire lumen, enables the treatment provider to select from a set of at least three usable length configurations, ready for use prior to, or during a medical procedure. The mandrel extending into a mandrel tip formed as a deflection surface, when positioned underneath the respective guide-wire exit ports, enables to systematically deflect the guide-wire passed through the catheter instrument at select positions of the catheter shaft.

Certain aspects of the subject matter of the present disclosure therefore may relate to a usable-length selectable catheter system (100), comprising:
a catheter (110); a lock-grip (120); and a mandrel with handle (130),
the catheter (110) further including a catheter tip (111); a balloon (112); a shaft (115); a kink protection sleeve (118); two or more guide-wire exit ports (131,116), located between the catheter tip and the tip of the kink-protection sleeve; and a manifold (119),
the manifold (119) further including an inflation port (1191); and a guide-wire port (1192),
the catheter shaft (115) further including an inflation lumen (1151) and a guide-wire lumen (1152); configured as a dual-lumen shaft (115),
the guide-wire lumen (1152) connecting the tip of the catheter (111) to the guide-wire port (1192) and the two or more guide-wire exit ports (113, 116);
the mandrel (130) including a tip (131) shaped as a deflection surface; a shaft (132); and a handle (135); the mandrel shaft (132) further including two or more surface markings (133, 134),
the mandrel shaft (132) optionally including an injection lumen (1321),
wherein the injection lumen (1321) passes straight through the mandrel tip (131); or alternatively,
wherein the injection lumen (1321) passes laterally through a surface of mandrel shaft (132),
wherein, when the mandrel is configured to comprise an injection lumen with lateral pass through, the catheter system is capable of passing a guide-wire distal, from a proximal guide-wire port through the injection lumen, and at substantially the same time, is capable of passing a guide-wire proximal, from a distal tip of a catheter, to at least one of the two guide-wire exit ports (113,116),
the deflection surface of the mandrel tip (131) optionally being shaped semispherical,
the mandrel tip (131) optionally being formed from a radiopaque material,
the smaller-outer-diameter shaft (132) of the mandrel being slideably moveable within a larger-outer-diameter guide-wire lumen (1152) of the catheter shaft (115),
the lock-grip (120) including a male luer connector (121); a first gripping surface (122); a second gripping surface (123); and a female luer connector (124),
the lock-grip (120), when attached to the catheter manifold (119) being capable of reversibly arresting the mandrel shaft in a position relative to the catheter shaft (115), the relative mandrel position being determined through shaft markings (133, 134) indicated to the treatment provider,
wherein, when the mandrel is positioned through the two or more shaft markings (133, 134), the mandrel tip (131) shaped as a deflection surface can deflect a guide-wire tip (140) such that the guide-wire exits at predetermined guide-wire exit ports (113, 116); or in the mandrels absence (1192),
wherein the described guide-wire deflection mechanism in combination with the position-indicated length-wise mandrel shaft locking within the guide-wire lumen (facilitated through the lock-grips' locking mechanism), enables the targeted selection of one port selected from the guide-wire port and the two or more guide-wire exit ports, thereby resulting in a set of at least three selectable usable lengths available for selection to a treatment provider, wherein the usable length is variably adjustable between a position of a (1) first and a second guide-wire exit port; and (2) a second guide-wire exit port and a tip of the kink-protection sleeve, wherein the length-lockable insertion of the mandrel into the catheter shaft, facilitated through the locking-mechanism of the lock-grip, enables the treatment provider to variably adjust the flexibility of the catheter shaft length-wise, thereby enhancing maneuverability and pushability of the catheter system, whereby the mandrel may in embodiments be referred to as a stiffening mandrel, wherein the mandrel enables the injection or aspiration of various diagnostic, therapeutic and/or body liquids, and, at substantially the same time, may serve as an alternate guide-wire lumen that facilitates the convenient exchange of guide-wires while leaving both the catheter and the inserted mandrel in place, and wherein, when the system is configured to comprise a mandrel with injection lumen with lateral pass through, a treatment provider is enabled to (1) pass a first guide-wire of 0.035 inch through the first guide-wire exit port 113; and, at substantially the same time, (2) pass a second guide-wire of 0.014 inch, from a port at the mandrel handle, through the second guide-wire exit port 116, thereby facilitating the use of two different sized guide-wires at substantially the same time.

Further embodiments of the catheter system according to the invention are described in the following items:

Item 1. A usable-length-selectable catheter system (100) comprising:
a catheter (110);
a lock-grip (120);
and a mandrel with handle (130).

Item 2. The catheter system of item 1, wherein the catheter comprises:
a catheter tip (111);
a balloon (112);
a shaft (115);
a kink protection sleeve (118);
two or more guide-wire exit ports (131,116), located between the catheter tip and the tip of the kink-protection sleeve; and
a manifold (119).

Item 3. The catheter system of item 1, wherein the lock-grip (120) comprises:
a male luer connector (121);
a first gripping surface (122);
a second gripping surface (123); and
a female luer connector (124).

Item 4. The catheter system of item 1, wherein the mandrel (130) comprises:
a tip (131) shaped as a deflection surface;
a shaft (132); and
a handle (135);

Item 5. The catheter system of item 2, wherein the manifold (119) further comprises:
an inflation port (1191); and
a guide-wire port (1192).

Item 6. The catheter system according to any preceding items, wherein the catheter shaft (115) further includes an inflation lumen (1151) and a guide-wire lumen (1152); configured as a dual-lumen shaft (115).

Item 7. The catheter system according to any preceding items, wherein the guide-wire lumen (1152) connects the tip of the catheter (111) to the guide-wire port (1192) and the two or more guide-wire exit ports (113, 116).

Item 8. The catheter system according to any preceding items, wherein the mandrel shaft (232) further includes two or more markings (133, 134).

Item 9. The catheter system according to any preceding items, wherein the mandrel shaft (132) further includes an injection lumen (1321).

Item 10. The catheter system according to any preceding items, wherein the two or more shaft markings (133, 134) provide visual, angiographic or haptic feedback to a treatment provider.

Item 11. The catheter system according to any preceding items, wherein the mandrel tip (131) is shaped as a semispherical deflection surface.

Item 12. The catheter system according to any preceding items, wherein the mandrel tip (131) is formed from a radiopaque material.

Item 13. The catheter system according to any preceding items, wherein the smaller-outer-diameter shaft (132) of the mandrel is slideably moveable within a larger-outer-diameter guide-wire lumen (1152) of the catheter shaft (115).

Item 14. The catheter system according to any preceding items, wherein the lock-grip (120), when attached to the catheter manifold (119), is capable of reversibly arresting the mandrel shaft (132) in a position relative to the catheter shaft (115).

Item 15. The catheter system according to any preceding items, wherein the mandrel shaft position relative to the catheter shaft (115) is indicated to the treatment provider by two or more shaft markings (133, 134).

Item 16. The catheter system according to any preceding items, wherein, when the mandrel is positioned through the two or more shaft markings (133, 134), the mandrel tip (131) shaped as a deflection surface deflects a guide-wire tip (140) such that the guide-wire exits at one of the two or more guide-wire exit ports (113, 116).

Item 17. The catheter system according to any preceding items, wherein the guide-wire deflection mechanism in combination with the position-indicated length-wise mandrel shaft locking within the guide-wire lumen enables the targeted selection of one port selected from the guide-wire port and the two or more guide-wire exit ports, thereby resulting in a set of at least three selectable usable lengths available for selection to a treatment provider.

Item 18. The catheter system according to any preceding items, wherein the length-lockable insertion of the mandrel into the catheter shaft, facilitated through the locking-mechanism of the lock-grip, enables the treatment provider to variably adjust the flexibility of the catheter shaft length-wise, thereby enhancing maneuverability and pushability of the catheter system.

Item 19. The catheter system according to any preceding items, wherein the mandrel enables the injection or aspiration of various diagnostic, therapeutic and/or body liquids, and, at substantially the same time, may serve as an alternate guide-wire lumen that facilitates the convenient exchange of guide-wires while leaving both the catheter and the inserted mandrel in place.

Item 20. The catheter system according to any preceding items, wherein the usable length is variably adjustable between a position of a (1) first and a second guide-wire exit port; and (2) a second guide-wire exit port and a tip of the kink-protection sleeve.

Item 21. The catheter system according to any preceding items, wherein the injection lumen (1321) passes straight through the mandrel tip (131).

Item 22. The catheter system according to any preceding items, wherein the injection lumen (1321) passes laterally through a surface of mandrel shaft (132).

Item 23. The catheter system according to any preceding items, wherein, when the system is configured to comprise a mandrel with injection lumen having a lateral pass through, a treatment provider is enabled to (1) pass a first guide-wire of 0.035 inch through the first guide-wire exit port 113; and, at substantially the same time, (2) pass a second guide-wire of 0.014 inch, from a port at the mandrel handle, through the second guide-wire exit port 116, thereby facilitating the use of two different sized guide-wires at substantially the same time.

Item 24. The catheter system according to any preceding items, wherein, when the mandrel is configured to comprise an injection lumen with lateral pass through, the catheter system is capable of passing a guide-wire distal, from a proximal guide-wire port through the injection lumen, and at substantially the same time, is capable of passing a guide-wire proximal, from a distal tip of a catheter, to at least one of the two guide-wire exit ports (113,116).

The invention claimed is:

1. A usable-length-selectable catheter system (100) comprising:
    a catheter (110) comprising a catheter shaft (115) and a kink protection sleeve (118);
    a lock-grip (120);
    a mandrel (130) with a handle; and
    two or more guide-wire exit ports (113, 116), disposed laterally at
    different axial positions of the catheter shaft (115);
characterized in that the mandrel (130) comprises a tip (131) shaped as a deflection surface that is configured to be selectively positioned relative to each one of the two or more guide-wire exit ports (113, 116) such that when a guide-wire (140) impinges on the deflection surface of the mandrel tip, the guide-wire can be reversibly guided through a selected guide-wire exit port;
    wherein a usable length of said catheter shaft is variably adjustable between a position of (1) a first and a second of said two or more guide-wire exit ports; and (2) said second guide-wire exit port and a tip of the kink-protection sleeve.

2. The catheter system according to claim 1, wherein the deflection surface of the tip (131) of the mandrel (130) is shaped semispherically.

3. The catheter system according to claim 1, wherein the mandrel (130) further includes a mandrel shaft (232) that includes two or more markings (133, 134).

4. The catheter system according to claim 3, wherein said two or more markings independently of each other provide visual, angiographic or haptic feedback to a treatment provider.

5. The catheter system according to claim 3, wherein said two or more markings (133, 134) are positioned on the mandrel shaft (232) such that they indicate whether the tip (131) of the mandrel (130) is positioned relative to a selected guide-wire exit port such that a guide-wire can be guided through the selected guide-wire exit port.

6. The catheter system according to claim 3, wherein the deflection surface of the mandrel tip (131) coordinates with a mechanism for locking the mandrel shaft within a guide-wire lumen disposed within the catheter shaft so as to enable targeted selection of one port selected from among at least one guide-wire entry port and said two or more guide-wire exit ports, to thereby, provide a set of at least three selectable usable catheter lengths available for selection to a treatment provider.

7. The catheter system according to claim 1, wherein the tip (131) of the mandrel (130) is formed from a radiopaque material.

8. The catheter system according to claim 1, wherein the catheter (110) further comprises:
    a catheter tip (111);
    a balloon (112); and
    a catheter manifold (119);
    wherein the two or more guide-wire exit ports (113,116) are located between the catheter tip and the tip of the kink-protection sleeve (118).

9. The catheter system according to claim 8, wherein the catheter manifold (119) comprises:
    an inflation port (1191); and
    a guide-wire port (1192).

10. The catheter system according to claim 8, wherein the lock-grip (120), when attached to the catheter manifold (119), is capable of reversibly arresting a shaft (132) of the mandrel in a position relative to the catheter shaft (115).

11. The catheter system according to claim 1, wherein the lock-grip (120) comprises:
    a male luer connector (121);
    a first gripping surface (122);
    a second gripping surface (123);
    a female luer connector (124), and
    a deformable cuff,
wherein, when the-twosaid first and second gripping surfaces (122, 123) of the lock-grip are mechanically engaged, the deformable cuff deforms such that the lock-grip yields a gripping force that arrests the mandrel shaft (232) in position.

12. The catheter system according to claim 1, wherein the catheter shaft (115) is configured as a dual-lumen shaft comprised of an inflation lumen (1151) and a guide-wire lumen (1152).

13. The catheter system according to claim 12, wherein the guide-wire lumen (1152) connects a tip (111) of the catheter to a guide-wire entry port (1192) and the two or more guide-wire exit ports (113, 116).

14. The catheter system according to claim 12, wherein a shaft (132) of the mandrel (130) has an outer diameter that is smaller than a diameter of the guide-wire lumen (1152) such that said mandrel shaft (132) is slideably moveable within the guide-wire lumen (1152).

15. The catheter system according to claim 1, wherein a shaft (132) of the mandrel (130) includes an injection lumen (1321).

16. The catheter system according to claim 15, wherein the injection lumen (1321) passes straight through the mandrel tip (131).

17. The catheter system according to claim 15, wherein the injection lumen (1321) passes laterally through a surface of the mandrel shaft (132).

18. The catheter system according to claim 1, wherein insertion of the mandrel into the catheter shaft by means of the lock-grip, enables a treatment provider to variably adjust flexibility of the catheter shaft length-wise, thereby enhancing maneuverability and pushability of the catheter system.

19. The catheter system according to claim 1, wherein the mandrel comprises an injection lumen (1321) that both enables injection or aspiration of various diagnostic, therapeutic and/or body liquids, and, at substantially the same time, serves as a guide-wire lumen (1321) that facilitates exchange of guide-wires while leaving both the catheter and the mandrel in place.

20. The catheter system according to claim 1, wherein said mandrel includes an injection lumen having a lateral pass through, which thereby enables a treatment provider to (1) pass a first guide-wire of about 0.035 inch through a first of said two or more guide-wire exit ports (113); and, at substantially the same time, (2) pass a second guide-wire of about 0.014 inch, from a port at the mandrel handle, through a second of said two or more guide-wire exit ports (116), thereby facilitating the use of two different sized guide-wires at substantially the same time.

21. The catheter system according to claim 1, wherein said mandrel includes an injection lumen with a lateral pass through, which thereby enables passing a guide-wire distally, from a proximal guide-wire entry port through the injection lumen, and at substantially the same time, enables passing a guide-wire proximally, from a distal tip of said catheter shaft, to at least one of the two or more guide-wire exit ports (113,116).

\* \* \* \* \*